US012644870B2

(12) United States Patent
Xia et al.

(10) Patent No.: US 12,644,870 B2
(45) Date of Patent: Jun. 2, 2026

(54) STERILIZATION INDICATOR SENSOR WITH A STERILANT-RESPONSIVE SWITCH

(71) Applicant: Solventum Intellectual Properties Company, Maplewood, MN (US)

(72) Inventors: Wensheng Xia, Woodbury, MN (US); Naiyong Jing, St. Paul, MN (US); G. Marco Bommarito, Stillwater, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 642 days.

(21) Appl. No.: 18/041,633

(22) PCT Filed: Aug. 17, 2021

(86) PCT No.: PCT/IB2021/057569
    § 371 (c)(1),
    (2) Date: Feb. 14, 2023

(87) PCT Pub. No.: WO2022/043828
    PCT Pub. Date: Mar. 3, 2022

(65) Prior Publication Data
    US 2023/0310685 A1     Oct. 5, 2023

Related U.S. Application Data

(60) Provisional application No. 63/071,482, filed on Aug. 28, 2020.

(51) Int. Cl.
    *G01N 31/22*      (2006.01)
    *A61L 2/28*       (2006.01)
    *G01N 27/02*      (2006.01)

(52) U.S. Cl.
    CPC .............. *G01N 31/226* (2013.01); *A61L 2/28* (2013.01); *G01N 27/02* (2013.01)

(58) Field of Classification Search
    CPC ........ A61L 2/28; G01N 27/02; G01N 27/126; G01N 31/226
    See application file for complete search history.

(56) References Cited

U.S. PATENT DOCUMENTS 5,863,465 A      1/1999   Kinlen
9,170,245 B2    10/2015   Landgrebe et al.
10,100,240 B2   10/2018   Callahan et al.
                (Continued)

FOREIGN PATENT DOCUMENTS

EP           2864769 B1     1/2019
WO      WO-2020217173 A1 * 10/2020   ......... G06K 19/0717

OTHER PUBLICATIONS

Chani, "Polyaniline based impedance humidity sensors", Solid State Sciences, Jan. 2013, vol. 18, pp. 78-82.
                (Continued)

*Primary Examiner* — Jennifer Wecker

(57)     ABSTRACT

A sensor device. The sensor device includes a sterilant-responsive switch comprising: a circuit; a conductive polymer having a first state and a second state, and a polymeric binder; and wherein the sterilant-responsive switch connects the circuit in the first state and disconnects the circuit in the second state, and wherein the conductive polymer is capable of being converted from being in the first state to being in the second state when in contact with a sterilant.

15 Claims, 5 Drawing Sheets

(56)                    References Cited

U.S. PATENT DOCUMENTS

| | | |
|---|---|---|
| 2004/0262170 A1 | 12/2004 | Centanni |
| 2005/0150778 A1* | 7/2005 | Lewis .................. G01N 33/497 |
| | | 204/403.01 |
| 2008/0025876 A1 | 1/2008 | Ramamurthy et al. |
| 2010/0230285 A1* | 9/2010 | Hoss .................... A61B 5/1473 |
| | | 600/347 |
| 2016/0178538 A1 | 6/2016 | Bommarito et al. |
| 2016/0363557 A1* | 12/2016 | Schenk ................ G01N 27/126 |
| 2018/0364188 A1* | 12/2018 | Ray ........................ C25D 11/00 |
| 2019/0357827 A1* | 11/2019 | Li ...................... A61B 5/14503 |
| 2021/0402033 A1* | 12/2021 | Ludowise .............. C12M 37/06 |

OTHER PUBLICATIONS

International Search Report for PCT International Application No.
PCT/IB2021/057569, mailed on Nov. 18, 2021, 5 pages.
Tables 1 of Guideline for Disinfection and Sterilization in Health-
care Facilities, Center for Disease Control, 2008, pp. 106-112.
Tables 7 of Guideline for Disinfection and Sterilization in Health-
care Facilities, Center for Disease Control, 2008, p. 119.

* cited by examiner

STERILIZATION INDICATOR SENSOR WITH A STERILANT-RESPONSIVE SWITCH

CROSS REFERENCE TO RELATED APPLICATIONS

This application is a national stage filing under 35 U.S.C. 371 of PCT/IB2021/057569, filed Aug. 17, 2021, which claims the benefit of U.S. Application No. 63/071,482, filed Aug. 28, 2020, the disclosure of which is incorporated by reference in its/their entirety herein.

BACKGROUND

Chemical indicators are widely used in sterilization monitoring to ensure the sterilization process has been completed correctly. Failed or insufficient sterilization cycles will put the patients in huge risk due to the potential cross-contaminations from the reprocessed surgical instruments.

Traditional chemical indicators are based on colorimetric changes in the presence of a certain sterilant and its running conditions such as sterilization temperature and sterilization time, etc. For example, a steam indicator may change color from light yellow to black. Another type chemical indicator such as Bowie-Dick test pack is designed to detect air leak or insufficient air removal in a sterilizer.

In the current practice of evaluating a chemical indicator visually, a user needs to visually judge the color development to determine if the chemical indicator was subjected to an adequate sterilization process. However, color development can be subjective. As a result, a better system is highly desirable.

SUMMARY

The sensor device can directly report the pass/fail information regarding each sterilization cycle to avoid any subject human eye color judgement to reduce errors. Also, the digitalization of chemical indicator will free people from manual document and physical storage.

In one aspect, the present disclosure provides a sensor device comprising: a sterilant-responsive switch comprising: a circuit; a conductive polymer having a first state and a second state, and a polymeric binder; and wherein the sterilant-responsive switch connects the circuit in the first state and disconnects the circuit in the second state, and wherein the conductive polymer is capable of being converted from being in the first state to being in the second state when in contact with a sterilant.

In another aspect, the present disclosure provides a method, the method comprising: providing the sensor device of the present disclosure; exposing the sensor device to a sterilant in a sterilization process; allowing the sterilant-responsive switch to react with the sterilant which changes the sterilant-responsive switch from the first state to the second state.

In another aspect, the present disclosure provides a system, the system comprising: the sensor device of the present disclosure; a memory element to store data captured by the sensor device; and a sensing device configured to interrogate the sensor device.

Various aspects and advantages of exemplary embodiments of the present disclosure have been summarized. The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

Definitions

For the following defined terms, these definitions shall be applied for the entire Specification, including the claims, unless a different definition is provided in the claims or elsewhere in the Specification based upon a specific reference to a modification of a term used in the following definitions:

The terms "about" or "approximately" with reference to a numerical value or a shape means +/–five percent of the numerical value or property or characteristic, but also expressly includes any narrow range within the +/–five percent of the numerical value or property or characteristic as well as the exact numerical value. For example, a temperature of "about" 100° C. refers to a temperature from 95° C. to 105° C., but also expressly includes any narrower range of temperature or even a single temperature within that range, including, for example, a temperature of exactly 100° C. For example, a viscosity of "about" 1 Pa-sec refers to a viscosity from 0.95 to 1.05 Pa-sec, but also expressly includes a viscosity of exactly 1 Pa-sec. Similarly, a perimeter that is "substantially square" is intended to describe a geometric shape having four lateral edges in which each lateral edge has a length which is from 95% to 105% of the length of any other lateral edge, but which also includes a geometric shape in which each lateral edge has exactly the same length.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

The terms "a", "an", and "the" include plural referents unless the content clearly dictates otherwise. Thus, for example, reference to a material containing "a compound" includes a mixture of two or more compounds.

"Ionic salt" refers to any salt having a cation selected from a group I, group II metal (particularly an alkaline earth metal), or post-transition metal. Preferably, magnesium or bismuth. The anions of an ionic salt can be selected from halogens, oxygen, sulfur, carbonate, borate, titanate, molybdate, phosphate, oxychloride, or combinations thereof.

"Integrated circuit" refers to a component that stores and processes information, in particular, a component that modulates and demodulates radio-frequency (RF) signals "Post-transition metal" refers to post-transition metals are a set of metallic elements in the periodic table located between the transition metals to their left, and the metalloids to their right. As suggested by, Huheey J E, Keiter E A & Keiter R L 1993, Principles of Structure & Reactivity, 4th ed., HarperCollins College Publishers, ISBN 0-06-042995-X, includes Ga, In, Tl, Sn, Pb, Bi, Al, Ge, Sb, Po.

"Second substrate position" refers to a position on the substrate that indicates adequate sterilization. May be established partially by the wicking substrate.

"Conductive element" refers to refers to an ability to conduct an electric current. Electrically conductive materials have an electrical conductivity of at least 2 Siemens per centimeter. Exemplary conductive elements include silver, gold, copper, aluminum, or combinations thereof.

"Monitoring loop" refers to an open or closed electrical loop.

"Adequate sterilization process" refers to a sterilization process that achieves a sterility assurance level of $10^{-6}$, or 12 log reduction of Bacillus Subtilis var. Niger. The sterility assurance level is related to a probability that a sterilized unit remains nonsterile after undergoing the sterilization process.

"Wicking" refers to any suitable material through which the organic compound can migrate by capillary action. Wicking substances can include paper strips, non-woven polymeric fabrics and inorganic fibrous compositions. Preferred wicking substances are Whatman No. 1 filter paper, Whatman No. 114 filter paper, PET fabric nonwoven, supported microcrystalline cellulose (TLC plate), supported aluminum oxide, and supported silica gel.

"Adequate environmental condition" refers to environmental conditions inside of a sterilization chamber that correspond to the adequate sterilization process.

"Conductive trace" refers to a conductive element forming part of an electrical circuit. Can also be a wire.

The phrase "comprises at least one of" followed by a list refers to comprising any one of the items in the list and any combination of two or more items in the list. The phrase "at least one of" followed by a list refers to any one of the items in the list or any combination of two or more items in the list.

Although the term "impedance" is used, the term "impedance" is the reciprocal of the "admittance". Depending on the context, either impedance or admittance can be used as changes in the impedance of a material also change the admittance of the material.

The term "and/or" means one or all of the listed elements or a combination of any two or more of the listed elements.

All numerical ranges are inclusive of their endpoints and nonintegral values between the endpoints unless otherwise stated (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

The disclosure may be more completely understood in consideration of the following detailed description of various embodiments of the disclosure in connection with the accompanying figures, in which.

While the above-identified drawings, which may not be drawn to scale, set forth various embodiments of the present disclosure, other embodiments are also contemplated, as noted in the Detailed Description. In all cases, this disclosure describes the presently disclosed invention by way of representation of exemplary embodiments and not by express limitations. It should be understood that numerous other modifications and embodiments can be devised by those skilled in the art, which fall within the scope and spirit of this disclosure.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

Unless otherwise indicated, all numbers expressing quantities or ingredients, measurement of properties and so forth used in the Specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Aspects of the present disclosure relate to a sensor device having a sterilant-responsive switch that is responsive to environmental conditions (including sterilant) in a sterilization process. The sterilant-responsive switch can be electrically coupled to conductive traces of the sensor device and can be mechanically activated or formed from a conductive polymer material.

Figure 1:
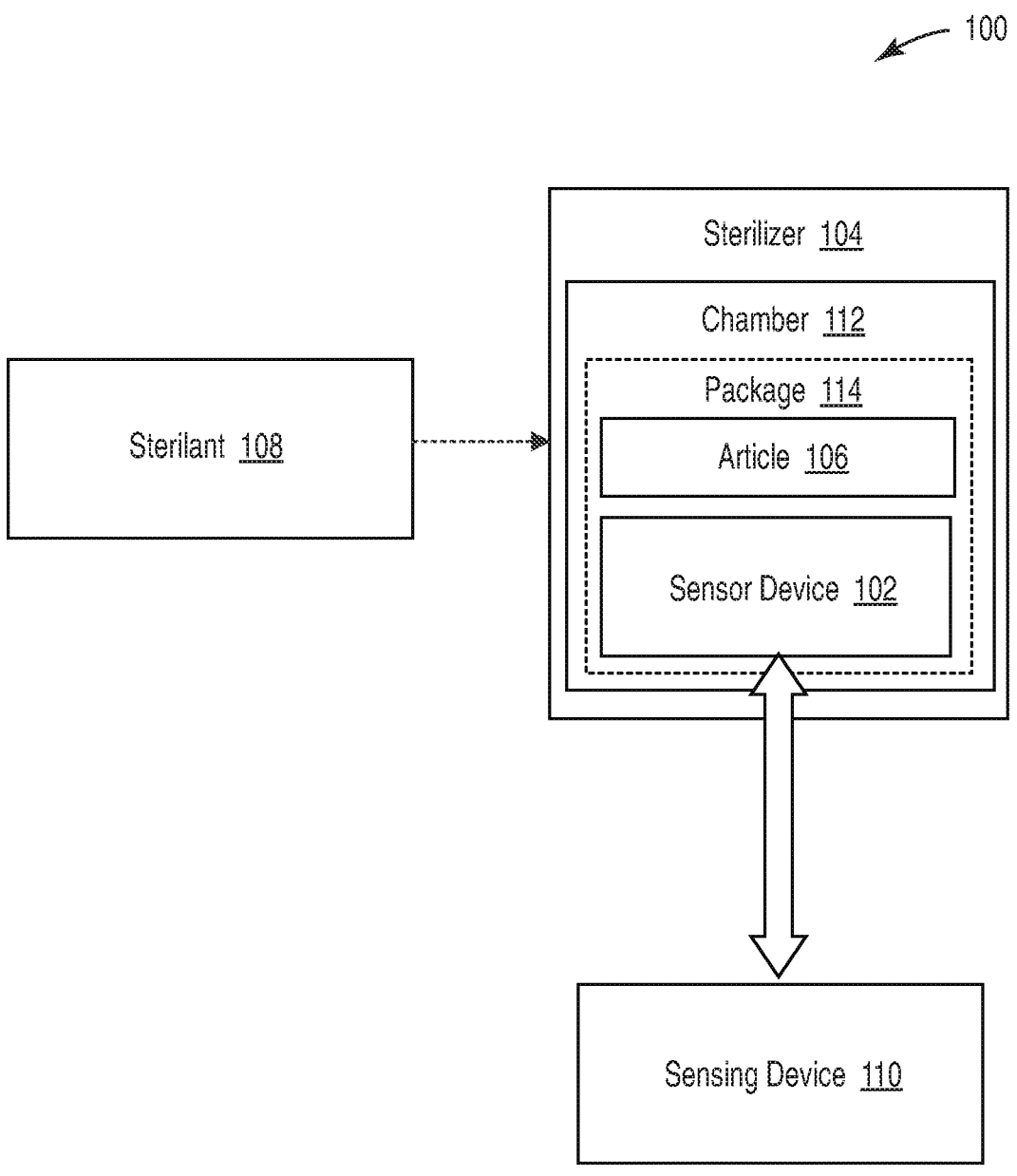
FIG. 1 illustrates a sterilization indicator system 100 in accordance with one embodiment.

FIG. 1 illustrates a sterilization indicator system 100. The sterilization indicator system 100 can include a sterilizer 104.

The sterilizer 104 is configured to provide a sterilant 108 to a chamber 112 in a sterilization process. Various examples of sterilizer 104 can exist and each sterilizer can differ as to the type of sterilant 108 provided. Sterilizer 104 can be based on steam, or hydrogen peroxide and each type can have different sterilization process conditions. Examples of sterilizers using hydrogen peroxide as a sterilant are commercially available from Steris (Mentor, OH) or Tuttnauer (Israel). Examples of sterilizers using steam as a sterilant are commercially available from Steris (Mentor, OH).

The chamber 112 can have one or more environmental conditions. In at least one embodiment, the environmental condition can be related to conditions inside of the chamber 112 and can include, but not limited to, exposure time, sterilant, temperature, pressure, or combinations thereof. For example, a first environmental condition can exist pre-sterilization process and a second environmental condition can exist during the sterilization process. A sensor device 102 can determine whether the second environmental condition corresponds to an adequate sterilization process. An adequate sterilization process can vary based on the sterilant used, the manufacturer of the sterilizer, and the article 106 to be sterilized. For example, Guideline for Disinfection and Sterilization in Healthcare Facilities, Center for Disease Control (2008) provides minimum cycle times for sterilization of various article 106 types and sterilant 108 in Tables 1 and 7, which are incorporated by reference.

The sterilization indicator system 100 includes a sensor device 102 that is capable of collecting and providing data regarding the environmental conditions within chamber 112 with respect to the sterilization process. Further, the sensor device 102 can also be read by a sensing device 110. The sensing device 110 is an electronic device that can read the environmental conditions remotely. In one example, the sensing device 110 can read the sensor device 102 to determine environmental conditions in the chamber 112 in real-time through the walls of the chamber 112. For example, a wall can have a hole formed therein for directly reading an RFID tag through the steel wall. In another example, the sensing device 110 can read/interrogate the sensor device 102 to determine environmental conditions of the chamber 112 when outside of the walls of the chamber 112, e.g., when in a wrapped package 114. In at least one embodiment, an adequate sterilization process can change the electrical impedance of the sensor device 102 and be detected by the sensing device 110.

The sensing device 110 can use wireless communication or wired communication to read the sensor device 102. For example, if wired, then the sensor device 102 can include a memory element to store the environmental conditions captured by the sensor device 102. In at least one embodiment, the sensor device 102 can be affected by past environmental conditions and be chemically or electrically modified. For example, the sensor device 102 can also include a sterilant-responsive switch that indicates, directly or indirectly, the environmental condition from the sterilization process in the chamber 112.

The sensor device 102 can include any type of sterilant-resistant integrated circuit. The sensor device 102 can include any appropriate electrical connection to communicate with a sensing device 110 that detects and measures any electrical signals generated. Such connections may, include, but are not limited to, hard wiring, physical electrical contacts, e.g., spring-loaded or jacks, Ethernet, Bluetooth, 802.11, wireless local area networks (WLANs), WiFi, WiMax and the like, or any other wired or wireless communication type known in the art.

For example, the sensor device can be an RFID tag, a thermometer, a pressure sensor, a communication device, or combinations thereof. In at least one embodiment, the sensor device 102 is an RFID tag and the sensing device 110 is an RFID interrogator device. Example RFID interrogator devices can be based on UHF and commercially available from Zebra (Lincolnshire, IL), Alien Technology (San Jose, CA), or Impinj (Seattle, WA). "Other example RFID interrogator device can also be based on High Frequency (HF) and commercially available from Jadak (Syracuse, NY), Technology Solutions Ltd (United Kingdom), Samsung, or Apple or be based on Low Frequency (LF) and commercially available from RFID Inc. (Aurora, CO), Gao RFID Inc. (Ontario, Canada), or SkyRFID Inc. (Ontario, Canada)."

The sensor device 102 can be paired with one or more components such as a substrate and environmental change receptor to form a sterilization indicator sensor which is described further herein. In at least one embodiment, the environmental change receptor is distinct from the sterilant-responsive switch. For example, the environmental change receptor can be configured to affect the admittance/impedance of the sterilant-responsive switch.

In at least one embodiment, the article 106 and sensor device 102 can be wrapped in a package 114. The sensor device 102 can be responsive to the sterilization process occurring in the chamber 112. The sensor device 102 can be read as to determine whether the using the sensing device 110 without unwrapping the package 114 which helps assure sterility of the article 106 to an end user.

Figure 2A:
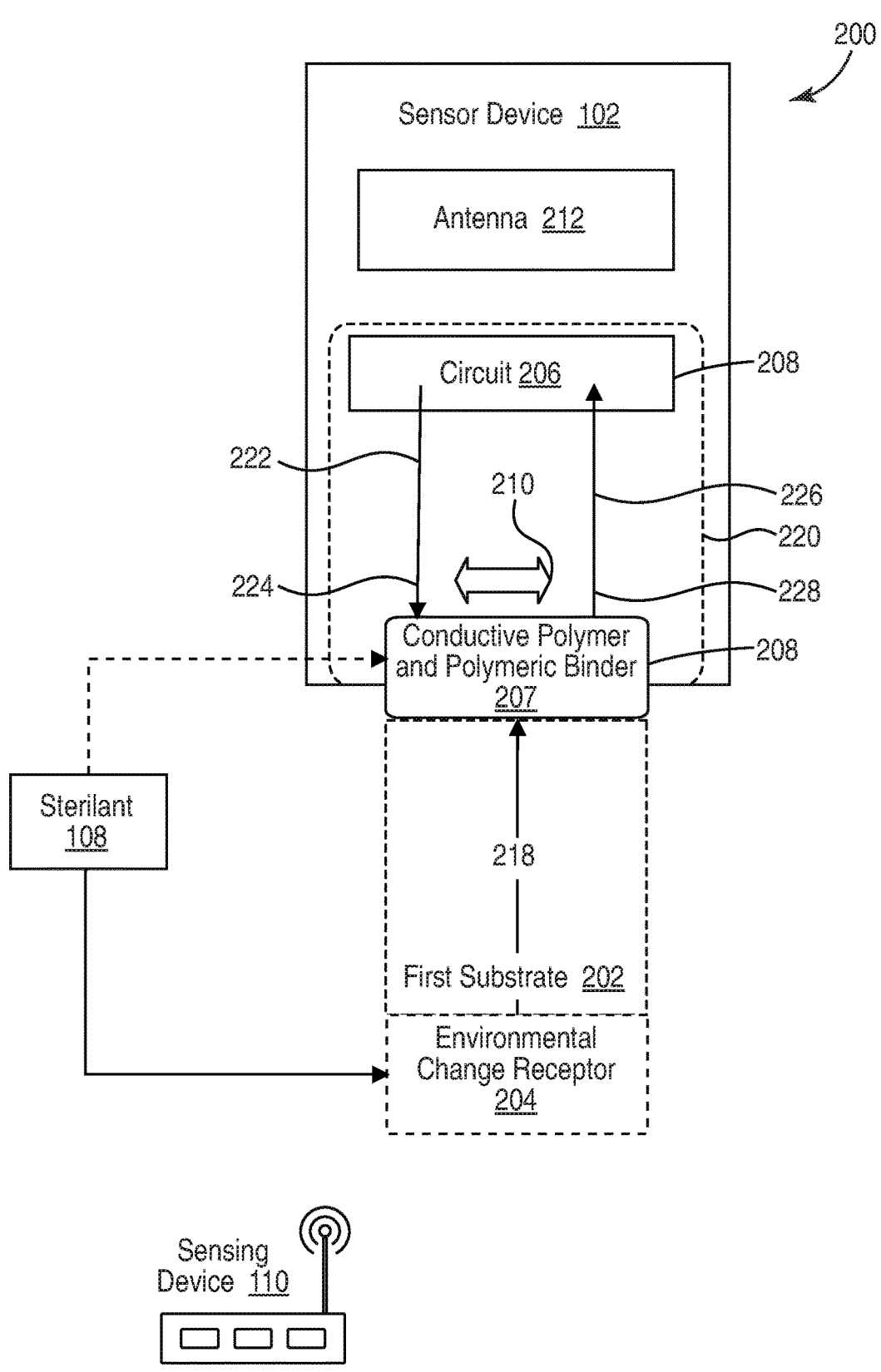
FIG. 2A illustrates a sterilization indicator sensor 200 in accordance with one embodiment.

FIG. 2A illustrates a sterilization indicator senso 200 for use in the sterilizer.

The sterilization indicator sensor 200 can include the sensor device 102 described herein. In at least one embodiment, the sensor device 102 can include a monitoring loop 220. The monitoring loop 220 can include the sterilant-responsive switch 208 which is electrically modifiable based on exposure to environmental conditions for the sterilization process, particularly an adequate sterilization process. In at least one embodiment, the monitoring loop 220 is configured to electrically change based on exposure to an adequate sterilization process. For example, the monitoring loop 220 can increase or decrease in admittance/impedance based on exposure to an adequate sterilization process.

The sterilant-responsive switch 208 can be based on a conductive polymer material or mechanical interaction with various components such as an environmental change receptor 204. In at least one embodiment, the sterilant-responsive switch 208 can include a circuit 206, a conductive polymer having a first state and a second state, and a polymeric binder (collectively, 207). In at least one embodiment, the sterilant-responsive switch 208 can be binary. For example, the sterilant-responsive switch 208 can be triggered from off to on indirectly based on interaction of the sterilant with environmental change receptor 204. In at least one embodiment, the circuit 206 can be an integrated circuit.

The sterilant-responsive switch 208 can also have a graduated response to the environmental condition. For example, a conductive polymer material may suffer from gradual electrical admittance degradation based on interaction from a sterilant 108. Examples of sterilant-responsive switch 208 are described further herein.

A conductive polymer material can be any substance that has semi-conductive properties or that is switchable between a first state and a second state. In other words, the conductive polymer is capable of being converted from being in the first state to being in the second state when in contact with a sterilant In at least one embodiment, the first state can be a first impedance state having a first impedance and the second state can be a second impedance state having a second impedance, for example, a solid substance that has conductivity between that of an insulator and a metal. In at least one embodiment, the impedance state can be related to the impedance and the admittance of the sensor device. The impedance state can be related to an opposition to flow of the conductive polymer material and include aggregation of its resistance, and inductive and capacitive reactances. In at least one embodiment, the first state can be a non-conductive state and the second state can be a conductive state and vice versa. The conductive state can be a doped conductive state and the non-conductive state can be a non-conductive reduced form or a non-conductive oxidized form of the conductive polymer. In at least one embodiment, the sterilant-responsive switch connects the circuit in the first state and disconnects the circuit in the second state.

The conductive polymer material can include an electrically active polymer that changes from a first impedance state to a second impedance state or a second impedance state to a first impedance state based on interactions with an environmental change receptor 204, an environmental condition, a conductive trace, or combinations thereof. In at least one embodiment, the first impedance state can either correspond to having higher or lower impedance relative to the second impedance state depending on the mechanism. For example, polyaniline can switch from non-conductive to conductive or vice versa. In at least one embodiment, the first impedance state refers to having an admittance and impedance sufficient to electrically bridge an open circuit, e.g., having an admittance of at least 2 siemens. The electrically active polymer can be a semi-flexible rod polymer. In at least one embodiment, the electrically active polymer can have a repeat unit of: aniline, acetylene, pyrrole, phenylene, phenylene vinylene, phenylene ethynylene, phenylene sulfide, fluorene, pyrene, azulene, napthalene, carbazole, indol, thiophene, ethylene dioxythiophene, or combinations thereof. The electrically active polymer can be doped or undoped with various dopants such as dinonylnaphthalene sulfonic acid (DNNSA), sodium, arsenic pentafluoride, triiodide, camphorsulfonate, methanesulfonic acid, halogens or polyhalogen ions, methanol, hydrogen sulfate, hydrochloric acid, tetrafluoroborate, sodium sulfite, or combinations thereof. Preferably, the conductive polymer material is polyaniline (PANI) which can be in one of three oxidation states (leucoemeraldine, emeraldine (in the salt or base forms), and per(nigraniline). The emeraldine can be non-conductive in the base form and conductive in the salt form. Further, the emeraldine salt can be converted into the leucoemeraldine salt or per(nigraniline) which are non-conductive, via a reduction reaction, when sterilant-responsive switch 208 in contact with steam or hydrogen peroxide. The conductive polymer can be converted to non-conductive polymer via a de-doping reaction, when sterilant-responsive switch 208 in contact with steam or hydrogen peroxide The polymeric binder can include any suitable binder, for example, a polyurethane, a polyvinyl butyral, a polyacrylate, polyvinyl acetate, polystyrene, polystyrene acrylate, a polyurea, a polyimide, an amide, an epoxy, a glycidyl-Si—Zr-containing solgel, a polyester, a phenoxy resin, a polysulfide, or mixtures thereof. With a polymeric binder, the reduced non-conductive PANI can maintain the non-conductive state much longer without going back (at least a year). It was found surprisingly without a binder, the conductive polymer material, can change from a first state to a second state, but the second state without a binder is reversable. For example, PANI can be reduced through the steam sterilization but the redox state of PANI without a binder is reversable, i.e. the non-conductive PANI can reverse back to the conductive PANI form quickly in the air. In addition, the conductive polymer, for example, PANI, can stick on metal surface but once it goes through the sterilization process, the reduced non-conductive PANI can be easily delaminated from the metal surface (chip away). In addition, when polymeric binder is used, the conductivity of PANI in a solid film can be significantly increased without an alcoholic wash. Thus, the alcoholic wash is optional when a binder is present and users can save cost and time without the additional step of alcoholic wash.

Further, the sensing device 110 can be configured to interrogate the sensor device 102 such that the sensor device 102 provides a plurality of impedance states over time which can correspond to various environmental conditions in the sterilization process. For example, the sensor device 102, when exposed to a first environmental condition, can transmit a first impedance state based on the interaction (direct or indirect) of the sterilant-responsive switch with the first environmental condition. An environmental condition can change the measured capacitance of the sterilant-responsive switch 208. The sensor device 102, when exposed to a second environmental condition, can transmit a second impedance state based on the interaction (direct or indirect) of the sterilant-responsive switch with the second environmental condition, and so forth with a third impedance state and a fourth impedance state. In at least one embodiment, the sensing device 110 can determine the environmental conditions based on the impedance states and provide a graduated view of the environmental conditions over time (as opposed to a binary pass/fail that may be present).

The sensor device 102 can include a first conductive trace 214 having a first end 222 and a second end 224 and a second conductive trace 216 having first end 226 and second end 228. The first ends of both conductive trace 214 and conductive trace 216 are electrically coupled to the circuit 206. In at least one embodiment, the second ends of conductive trace 214 and conductive trace 216 are not integrally attached using the same material as that of conductive trace 214 or conductive trace 216. In at least one embodiment, the second ends of conductive trace 214 and conductive trace 216 can each be connected through a sterilant-responsive switch 208. In at least one embodiment, the conductive traces can also include adjacent microreplicated channels for capillary flow parallel to the conductive trace.

In at least one embodiment, the distance 210 between conductive trace 214 and conductive trace 216 as measured along a sterilant-responsive switch 208. The distance 210 can be sufficient to sense a change in the electrical admittance/impedance without causing electrical shorts or interference between the conductive trace 214 and conductive trace 216. For example, if the distance 210 is zero, then conductive trace 214 and conductive trace 216 would be electrically coupled regardless of changes in the sterilant-responsive switch 208 and the monitoring loop 220 would not sense the environmental condition.

In at least one embodiment, the conductive trace 214 and conductive trace 216 can include a metal electrode, for example, coated with or formed from a conductive material. The metal electrode can include a metal and the oxidation potential of the metal is greater than the reduction potential of the conductive polymer. Example if suitable metal can include aluminum, iron, zinc, tungsten, molybdenum, tin, nickel, copper, semiconductive metals or alloys thereof. For example, the use of aluminum has been surprisingly found to directly react with PANI and convert emeraldine salt into leucoemeraldine salt. The monitoring loop 220 can thus turn from a first impedance state to a second impedance state based on the redox reaction of the conductive polymer material with the metal at the environmental condition corresponding to an adequate sterilization process (e.g., of steam).

In at least one embodiment, the sterilization indicator sensor 200 can include only the sensor device 102. The sterilization indicator sensor 200 can also optionally include the first substrate 202 and/or the environmental change receptor 204.

In at least one embodiment, a portion of the sterilant-responsive switch 208 can contact the first substrate 202. The first substrate 202 can be either wicking or non-wicking. If non-wicking, the first substrate 202 can be any metallic layer such as aluminum foil, or polymeric layer such as polyethylene, polyurethane, or polyester layer. In at least one embodiment, the first substrate 202 can provide structural support to the sensor device 102. The first substrate 202 can also provide support to the environmental change receptor 204.

If wicking, the first substrate 202 can be any suitable material through which the organic compound can migrate by capillary action. The preferred wicking first substrate 202 is a paper strip. Other such wicking materials such as non-woven polymeric fabrics and inorganic fibrous compositions may be used. The dimensions of the wicking first substrate 202 is not critical. However, its dimensions (thickness and width) will affect the rate of wicking and determine the quantity of organic compound required to result in a suitable scale length. Hence, from an economic standpoint the wicking first substrate 202 should be as thin as practical. A suitable width for the first substrate 202 is about $\frac{3}{16}$ to about $\frac{1}{4}$ of an inch. Examples of the wicking first substrate 202 are Whatman No. 1 filter paper, Whatman No. 114 filter paper, supported microcrystalline cellulose (TLC plate), supported aluminum oxide, and supported silica gel.

In at least one embodiment, the environmental change receptor 204 is disposed proximate the first substrate 202. For example, the environmental change receptor 204 can be positioned such that the environmental change receptor 204 flows onto the first substrate 202 and is wicked from a first substrate position to a second substrate position (which may correspond to a portion of the sterilant-responsive switch 208) as indicated by flow direction 218. In at least one embodiment, the environmental change receptor 204 can also be disposed directly on the first substrate 202 at the first substrate position. In at least one embodiment, the environmental change receptor 204 is disposed proximate or adjacent to the sterilant-responsive switch 208. In at least one embodiment, the environmental change receptor 204 is solid and can be in the form of a tablet and disposed outside of the first substrate 202. In at least one embodiment, the environmental change receptor 204 can be embedded within or layered upon the first substrate 202.

The environmental change receptor 204 can include one or more environmentally responsive or sensitive materials selected depending on the sensing needs. The environmentally responsive material can be selected based on its solubility, boiling point, melting point, ability to absorb gases or liquids, softening point or flow properties, such that it changes properties (evaporates or redistributes on the sensor strip) in response to specific environmental conditions. In some cases, the environmental change receptor 204 can include more than one part, where each part can include similar or different environmentally responsive materials and be disposed at different locations. In at least one embodiment, the environmental change receptor 204 can be selected based on an ability to change the admittance/impedance of the sterilant-responsive switch. The environmental change receptor 204 can be acidic or basic to affect the first impedance state of a conductive polymer material. For example, if the environmental change receptor 204 is basic, then the base can react with emeraldine salt to form emeraldine base and change from a first impedance state to a second impedance state.

The environmental change receptor 204 can include a type of meltable or flowable material, for example, crystalline or semi-crystalline materials (e.g., Tetra-n-butylammonium bromide (TBAB)), thermoplastics, polymers, wax, organic compounds such as salicylamide, polyethylene-co-acrylic acid, sucrose and the like. In some cases, the environmentally responsive material is selected based on its response to combined conditions of temperature and humidity, or temperature, humidity and time. The material can be selected to tailor to a particular application. In some embodiments to monitor the presence of chemical substance, the environmental change receptor 204 can include a type of material absorbing or reacting with the chemical substance. In an example of detecting gas, the environmental change receptor 204 can include Zeolite HiSiv 3000 powder from UOP LLC, Des Plaines, IL.

Some environmental change receptors can be responsive to a steam sterilant in environmental conditions for an adequate sterilization process. In at least one embodiment, the environmental change receptor 204 can include an organic base having a melting point of greater than 100 degrees C. and miscible with salicylamide. For example, the organic base can be N,N-dimethylpyridine, adamantylamine, or combinations thereof.

Some environmental change receptors can also be responsive to a steam or hydrogen peroxide sterilant in an adequate sterilization process. Such an environmental change receptor can include various pigments and inks such as a blue colored ink and a pink pigment. Further the environmental change receptor can include an organic ester that is solid at room temperature. In at least one embodiment, the sterilant 108 can interact with environmental change receptor 204, sterilant-responsive switch 208, or both to produce a change which would affect sensor device 102.

The sensor device 200 can include an antenna 212 which is capable of receiving energy from and transmitting data to a sensing device 110. Antenna 212 can be various shapes that are optimized for transmission to the sensing device 110. One example of an antenna 212 design is commercially available from Smartrac (Netherlands) under the Model name BELT.

In at least one embodiment, the antenna 212 can be formed such that it is unaffected by the sterilization process. For example, the antenna 212 can have no breaks within an antenna loop (but the sensor device 102 may have a break within the monitoring loop 220). The antenna 212 can be electrically coupled to the integrated circuit 206 and form the antenna loop. The integrated circuit 206 can harvest energy from the sensing device 110 to transmit the antenna 212 impedance. Various integrated circuit 206 devices can be designed for RFID applications, such as passive, semi-active, and active RFID applications, and commercially available from NXP Semiconductors (Netherlands), Impinj (Seattle, WA), or Axzon (Austin, TX). An example of the integrated circuit 206 is under the trade designation Magnus from Axzon (Austin, TX) or the UCODE G2iM or G2iL+ from NXP Semiconductors which can include UHF RFID transponder capability and a tag tamper alarm capable of measuring the state of the monitoring loop 220.

In at least one embodiment, the sensor device 200 can include a second integrated circuit responsive to a different frequency than the first integrated circuit. The second integrated circuit can be electrically coupled to the antenna 212 or a second antenna. The second integrated circuit can also be electrically coupled to the monitoring loop.

Figure 2B:
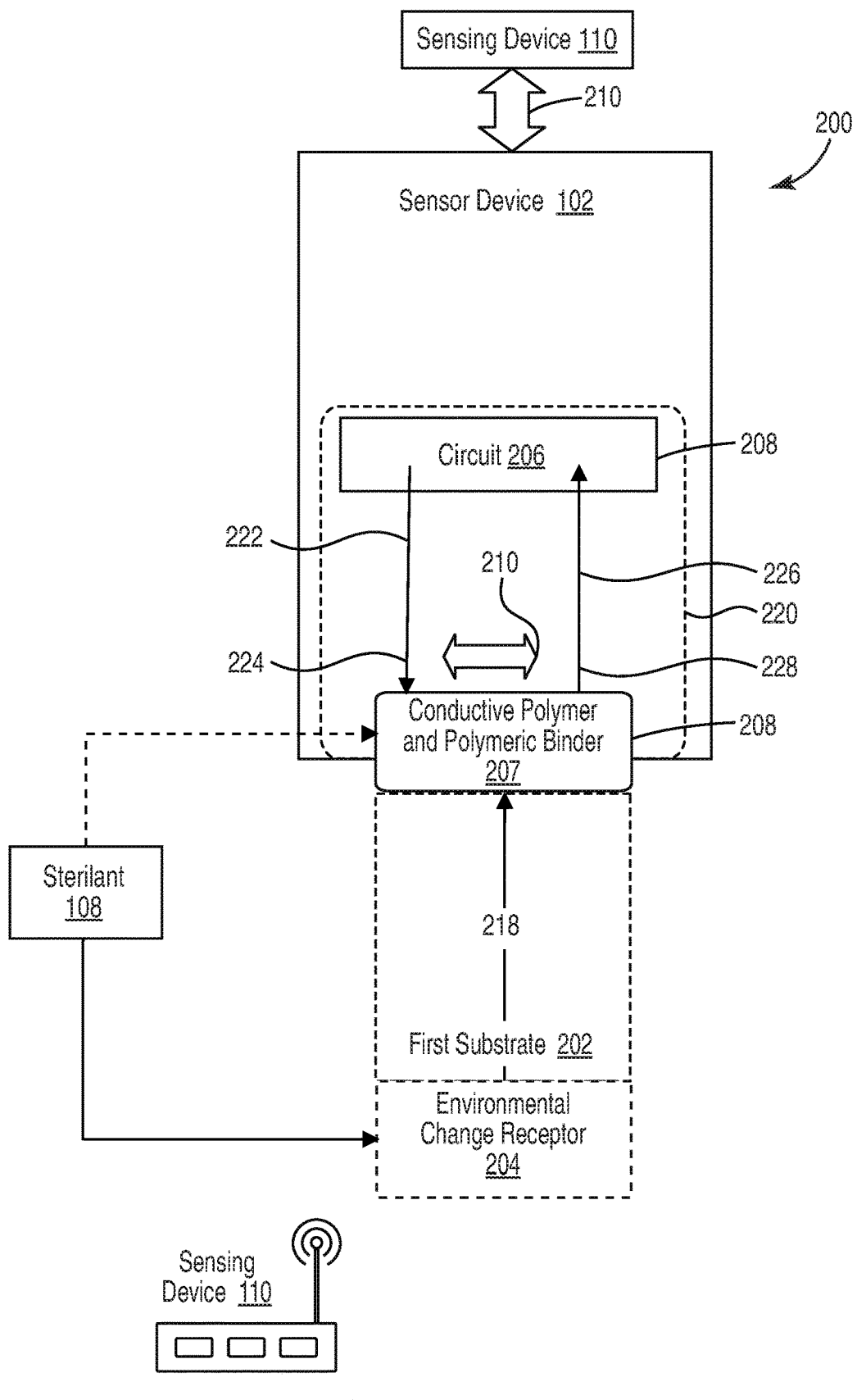
FIG. 2B illustrates an alternative sterilization indicator sensor 200 in accordance with one embodiment.

FIG. 2B illustrate a sterilization indicator sensor 200 that is similar to sterilization indicator sensor 200 of FIG. 2A except that the circuit 206 is read through a direct physical contact with the sensing device 110 for impedance or resistance measurement. The direct physical contact can be a hard-wired electrical connections 250 between the electrodes and the electrical circuit used to detect and measure the electrical signal resulting from electron transfer.

Figure 3:
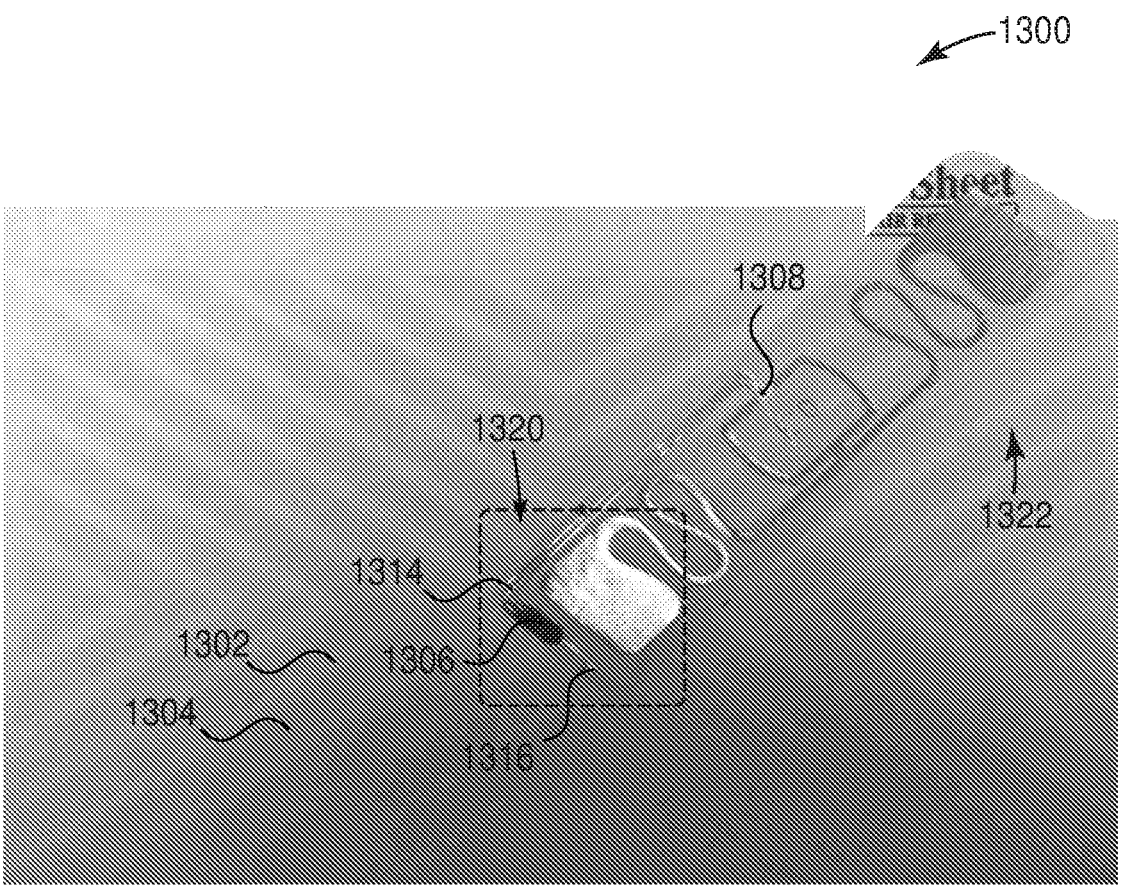
FIG. 3 illustrates a sterilization indicator sensor 1300 at a different view.

FIG. 3 illustrates a sterilization indicator sensor 1300 at a different view. The conductive trace 1314 and conductive trace 1316 are shown contacting the polymeric gate material

1306. Once exposed to a sterilant, the polymeric gate material 1306 can change admittance/impedance which is sensed by an RFID interrogator device.

In at least one embodiment, the sterilization indicator sensor 1300 can be present in a stack of cards which can generally be paper or formed from the first substrate. The sterilization indicator sensor 1300 can be structurally similar to the chemical indicator described in U.S. Pat. No. 9,170, 245 which is incorporated by reference. In at least one embodiment, the stack of cards can have the sterilization indicator sensor 1300 positioned medially in the stack of cards.

In at least one embodiment, the sterilization indicator sensor 1300 can form a central zone 1320 and a peripheral zone 1322. Peripheral zone 1322 can surround a central zone 1320. In at least one embodiment, the central zone 1320 can have only partial contact with the sterilant occurred when placed in the stack of cards. The central zone 1320 can be a result of an air pocket formed by the stack of cards with sterilization indicator sensor 1300. In at least one embodiment, the central zone can mirror the shape of the sterilization indicator sensor 1300. For example, the central zone 1320 can be a rectangular (such as a rhomboid), or elliptical shape. In one example, the sterilization indicator sensor 1300 has an area of no greater than 25 square inches and a central zone 1320 of no greater than 1 square inch. Thus, the ratio of overall area to the central zone area can be no greater than 25:1.

In at least one embodiment, the air pocket can be representative of a challenge path that is sterilized last. In at least one embodiment, the polymeric gate material 1306 is positioned in the geometric center of the first substrate 1302 and/or the central zone such that the polymeric gate material 1306 detects whether an adequate environmental condition occurs in the central zone. For example, sterilant can interact with the peripheral zone 1322 but may take time to interact with the central zone 1322 when packaged in the stack of cards. As shown, the polymeric gate material 1306 contacts the ionic salt 1304.

In at least one embodiment, the stack can be completely wrapped in a sheet of material to form a wrapped package. For example, the sheet of material can be a nonwoven that can be a sterilant-permeable medical wrapping commercially available as a sterilization wrap.

Figure 4:
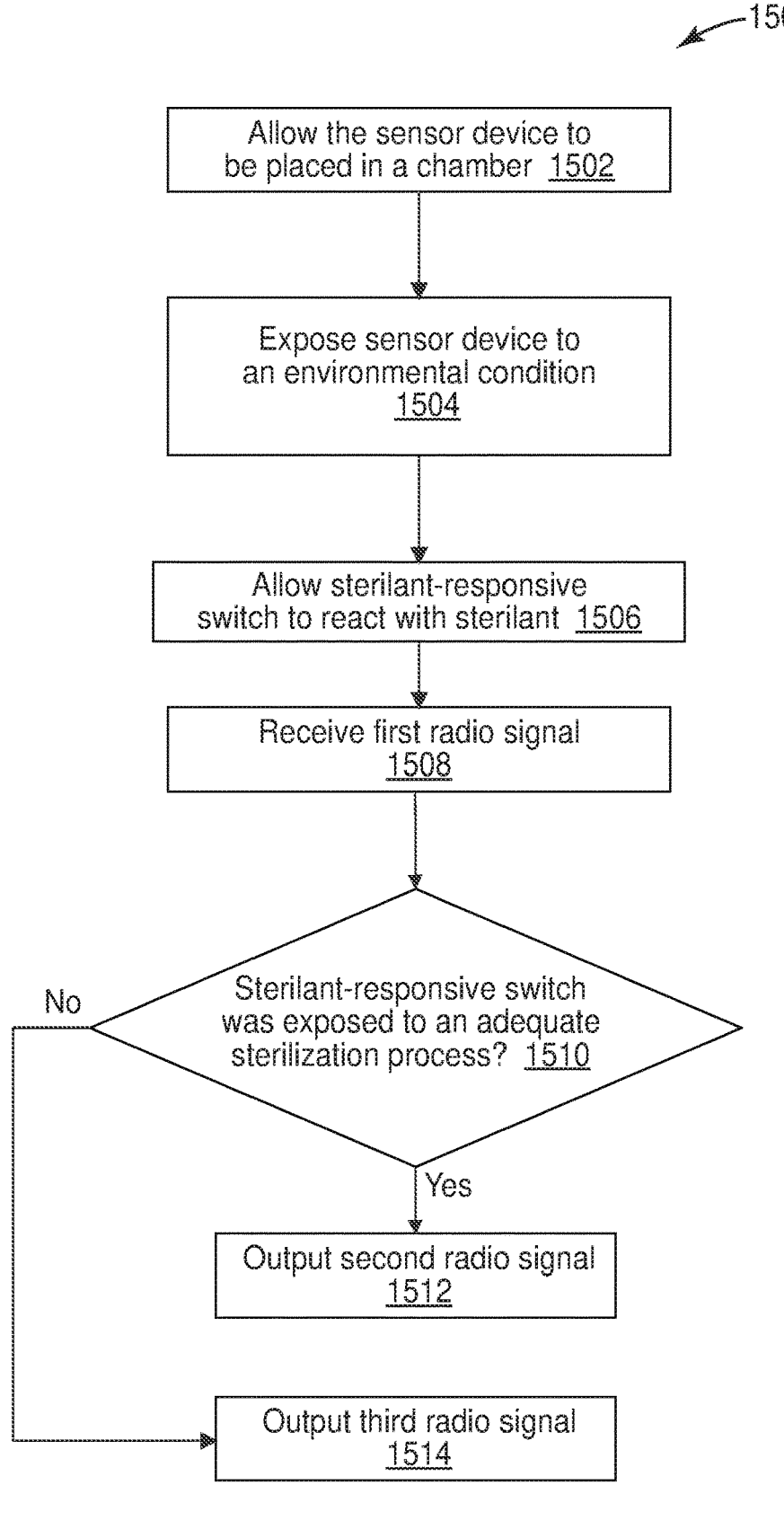
FIG. 4 illustrates a method 1500 in accordance with one embodiment.

FIG. 4 illustrates a method 1500 of using the sensor device.

The method 1500 can begin at block 1502. In block 1502, a user can place the sensor device in the chamber of a sterilizer. In at least one embodiment, the user can place the sensor device with an article to be sterilized in the chamber. The user can also package the sensor device and the article in a wrapped package such that the sensor device is not visible while the package is wrapped. The sensor device is described further herein and includes a sterilant-responsive switch. In at least one embodiment, the user can place the sensor device can be a part of a sterilization indicator sensor which can be placed in the chamber. After the sensor device is placed in the chamber, then the chamber can be sealed from the environment.

In block 1504, a user can activate a sterilization process of the sterilizer and the sensor device can be exposed to a sterilant and/or one or more environmental conditions in a sterilization process. For example, if the sterilant is steam, then the sterilant is at least 95% saturated steam/water vapor and the sterilization process is 134 degrees Celsius for 2 minutes or 121 degrees Celsius for 10 minutes. In another example, if the sterilant is hydrogen peroxide, then the environmental condition is an atmosphere containing 31% hydrogen peroxide vapor and the sterilization process is 50 degrees C. for 60 minutes. Various standards for each sterilant can exist and may vary based on the manufacturer, article to be sterilized, or combinations thereof. In at least one embodiment, the environmental condition includes the presence of the sterilant.

In block 1506, the sterilant-responsive switch of the sensor device or the sterilization indicator sensor can react with the sterilant or react (physically or chemically) with the environmental condition (which can include the sterilant). In at least one embodiment, the sterilant-responsive switch can also interact with a substrate or an environmental change receptor to modify the admittance/impedance of the sterilant-responsive switch. For example, the environmental condition, environmental change receptor, or combinations thereof, can cause sterilant-responsive switch to change from the first state to the second state, for example, from a first impedance state to a second impedance state, or vice versa.

In block 1508 through block 1514, a sensing device can be configured to read the sensor device to determine whether the first impedance state is present.

In at least one embodiment, the sensing device is configured to read the sensor device through a wrapped package. The sensing device can also be configured to read the sensor device when the chamber is sealed (i.e., through a housing of the sterilizer). The sensing device can use an onboard memory to later read the sensor device. In at least one embodiment, the sensing device can be an RFID interrogator device. The sensing device can be configured to transmit a first radio signal to the sensing device in block 1508. The first radio signal can be a variety of frequencies but is preferably UHF (300 MHz-3000 MHz).

The first radio signal can affect the sensor device and the sensor device can emit a second radio signal or a third radio signal in block 1512, or block 1514. For example, in decision block 1510, if the sterilant-responsive switch was exposed to a sterilization process, for example, an adequate sterilization process, then the sensor device can output a second radio signal in block 1512. If the sensor device was not exposed to an adequate sterilization process, then the sensor device can output a third radio signal in block 1514. In at least one embodiment, the output can be inherent and not require any computational resources of the sensor device. In at least one embodiment, the second radio signal can be indicative of whether the sterilant-responsive switch has degraded (e.g., the sterilant cause degradation of the sterilant-responsive switch directly or indirectly). In at least one embodiment, the second radio signal can be indicative of whether the sterilant-responsive switch completed a circuit of a monitoring loop of the sensor device. The third radio signal can be indicative of no degradation or minimal degradation of the sterilant-responsive switch.

The presence of the second or third radio signal can indicate to the sensing device whether the sensor device was exposed to environmental conditions from an adequate sterilization process. The sensing device can further communicate whether the adequate sterilization process was achieved and perform subsequent actions as a result.

LIST OF ILLUSTRATIVE EMBODIMENTS

1. A sensor device comprising: a sterilant-responsive switch comprising: a circuit; a conductive polymer having a first state and a second state, and a polymeric binder; and wherein the sterilant-responsive switch connects the circuit in the first state and disconnects the circuit in the second state, and wherein the conductive polymer is capable of being converted from being in the first state to being in the second state when in contact with a sterilant.

2. The sensor device of embodiment 1, wherein the conductive polymer changes from a first impedance to a second impedance when an environmental change receptor or the sterilant contacts the conductive polymer.

3. The sensor device of any of embodiments 1 to 2, wherein the conductive polymer comprises a repeat unit of: aniline, acetylene, pyrrole, phenylene, phenylene vinylene, phenylene ethynylene, phenylene sulfide, fluorene, pyrene, azulene, napthalene, carbazole, indol, thiophene, ethylene dioxythiophene, or combinations thereof.

4. The sensor device of any of embodiments 1 to 3, wherein the conductive polymer comprises a repeat unit of aniline, pyrrole, or combinations thereof.

5. The sensor device of any of embodiments 1 to 4, further comprising a first conductive trace and a second conductive trace, each having a first end electrically coupled to the circuit and a second end.

6. The sensor device of embodiment 5, wherein the sterilant-responsive switch modifies an electrical connection between the first conductive trace and the second conductive trace in response to a sterilization process.

7. The sensor device of embodiment 5, wherein the first conductive trace and the second conductive trace comprise a metal electrode.

8. The sensor device of embodiment 7, wherein the metal electrode comprises a metal, wherein the oxidation potential of the metal is greater than the reduction potential of the conductive polymer.

9. The sensor device of embodiment 7, wherein the metal electrode comprises aluminum, iron, zinc, tungsten, molybdenum, tin, nickel, copper, or alloys thereof.

10. The sensor device of embodiment 7, upon exposure to an adequate environmental condition comprising a steam sterilant, the metal electrode reacts with the conductive polymer to change impedance of the conductive polymer.

11. The sensor device of any of embodiments 1 to 10, wherein the sterilant-responsive switch is configured to change impedance in response to an adequate sterilization process.

12. The sensor device of any of embodiments 1 to 11, wherein the circuit is an integrated circuit.

13. The sensor device of any of embodiments 1 to 12, wherein polymeric binder comprises a polyurethane, a polyvinyl butyral, a polyacrylate, polyvinyl acetate, polystyrene, polystyrene acrylate, a polyurea, a polyimide, an amide, an epoxy, a glycidyl-Si—Zr-containing solgel, a polyester, a phenoxy resin, a polysulfide, or mixtures thereof.

14. The sensor device of any of embodiments 1 to 13, wherein the conductive polymer is undoped.

15. The sensor device of any of embodiments 1 to 14, wherein the conductive polymer is doped with a dopant.

16. The sensor device of any of embodiments 1 to 15, wherein the first state results in a closed monitoring loop.

17. The sensor device of any of embodiments 1 to 16, wherein the second state is non-conductive.

18. The sensor device of any of embodiments 1 to 17, wherein the sterilant comprises steam or water.

19. The sensor device of any of embodiments 1 to 18, wherein the environmental change receptor comprises salicylamide.

20. The sensor device of any of embodiments 1 to 19, wherein the environmental change receptor comprises an organic base having a melting point of greater than 140 degrees C. and miscible with salicylamide.

21. A method, the method comprising:
   providing the sensor device of any one of embodiments 1 to 20;
   exposing the sensor device to a sterilant in a sterilization process;
   allowing the sterilant-responsive switch to react with the sterilant which changes the sterilant-responsive switch from the first state to the second state.

22. The method of embodiment 21, wherein the sterilant is at least 95% saturated steam and the adequate sterilization process is 134 degrees Celsius for 2 minutes or 121 degrees Celsius for 10 minutes.

23. The method of embodiment 21, wherein the sterilant is hydrogen peroxide and an atmosphere of the environmental condition contains 31% hydrogen peroxide vapor and the sterilization process is 50 degrees C. for 60 minutes.

24. A system, the system comprising:
   the sensor device of any one of embodiments 1 to 20;
   a memory element to store data captured by the sensor device; and
   a sensing device configured to interrogate the sensor device.

The following working examples are intended to be illustrative of the present disclosure and not limiting.

EXAMPLES

Materials

Tamper evident RFID Inlays (Smartrac Technology Group, Irvine, CA)
Polyaniline (Boron Molecular, Raleigh, North Carolina)
Desmodur N3300 (Covestro LLC, Pittsburgh, PA)
Desmodur N3390 (Covestro LLC, Pittsburgh, PA)
CAPA 3031 (Perstorp Polyols Inc., Toledo, OH)
T-12 Catalyst (Evonik Corp., Parsippany, NJ)
RFID Reader (ThingMagic, Woburn, MA)
COMPLY Bowie-Dick Test Pack (3M Company, St. Paul, MN)
Electric Multimeter (Fluke, 89IV)
Xylene
MIBK

Example 1. Electrical Resistance Study

A stock 50% dinonylnaphthalene sulfonic acid-doped polyaniline (polyaniline:DNNSA=1:1.5) solution in toluene was further diluted to 30% (w/w) in toluene for preparing the coating solutions. Polyisocyanate was diluted by a mixture of 50%/50% xylene and methylisobutylketone (MIBK) or toluene to the desired concentration listed in Table 1. Polyol was also diluted to the desired concentration shown in Table 1 in a mixture of 50/50 of xylene and MIBK or in MIBK. The coating solutions were compounded at room temperature and coated using a #22 Meyer bar onto 5 mil polyethylene terephthalate (PET) film and then cured at 140° C. for 10 minutes (min). Conductivity of the coated film was measured using a multimeter (Fluke, 89IV) with two probes one-inch distance apart. In some cases, the film was dipped into methanol for 10 seconds and again dried at 140° C. for 5 min before electric resistance measurement were taken. Resistance measurements and coating observations are reported in Table 1.

TABLE 1

Formulations and coating properties.

| Ingredient Mass (g) | Formulations | | | | | | |
|---|---|---|---|---|---|---|---|
| | 1 | 2 | 3 | 4 | 5 | 6 | 7 |
| 1 1.642 | 30% PANI 30% Desmodur 3390 | 30% PANI 25% Desmodur 3390 | 35% PANI 25% Desmodur 3390 | 30% PANI 20% Desmodur 3390 | 30% PANI 25% Huntsman 5180A | 30% PANI N/A | 30% PANI N/A |
| 0.637 | 30% CAPA 3031 | 25% CAPA 3031 | 25% CAPA 3031 | 20% CAPA 3031 | 25% Huntsman 8180B | N/A | N/A |
| 0.012 | T-12 catalyst | T-12 catalyst | T-12 catalyst | T-12 catalyst | T-12 catalyst | T-12 catalyst | T-12 catalyst |
| 1 | | | | | | 20% Huntsman 5180A | 15% Huntsman 5180A |
| 1.271 | | | | | | 20% Huntsman 8180B | 15% Huntsman 8180B |
| 0.318 | MIBK/ Xylene (1:1) | MIBK/ Xylene (1:1) | MIBK/ Xylene (1:1) | MIBK/ Xylene (1:1) | Toluene | Toluene | Toluene |
| Resistance (MΩ) | >50M | 0.3 | 0.6 | 0.6 | N/A | 8 | 3.5 |
| Resistance after IPA wash (MΩ) | >50M | 0.3 | 0.6 | 0.3 | | 1 | 0.3 |
| Note | Hazy coating | | | | Solution unstable | | |

Example 2. Electrical Resistance in Bowie-Dick Test Pack

The same procedure was used to make coated film samples with the coating solutions shown in Table 2. The solutions were coated on a 3 mil PET film on which were printed two 1-mm aluminum wires separated by 1 cm. A #22 Meyer bar was used to apply the coating. An adhesive and release liner had been applied to the back of the PET film prior to coating. The coated samples were cured at 140° C. for 10 minutes. The samples were then dipped into methanol for 10 seconds and dried at 140° C. for 5 minutes. As a control, the same solution was coated on 3-mil PET without printed aluminum wires using the same coating procedure. The coated samples were cut into approximately 8 mm×20 mm strips, the release liner was removed, and the coated film strips were adhered to a paper card from a Comply™ Bowie-Dick test pack (3M Company, St. Paul). Six coated film strips were adhered to the card starting from the center of the card and extending to upper-left corner along the diagonal line as shown in FIG. 1. The resistance between the two wires of each coated film strip was measured for each coated film strip. The resistance of each strip was about 0.3 MΩ. The card was then inserted into a Comply™ Bowie-Dick test pack, replacing the card facing the chemical indicator sheet (the chemical indicator sheet was also removed). The stack of cards was re-wrapped and sterilized at two different conditions: an ISO INADQ pass cycle (132° C., 3.5 minutes with vacuum to 24 inHg and pressure at 26 psi) and an ISO INADQ fail cycle (132° C., 3.5 minutes with vacuum to 10 inHg and pressure at 10 psi). For each experiment, an unmodified Comply™ Bowie-Dick test pack was used as a control. After the sterilization cycle was completed, the modified test pack was immediately removed from the sterilizer and the electric resistance between the two printed aluminum wires of each coated film strip were measured. Table 3 shows the resistance of coated film strips with printed aluminum wires in fail cycles using three different coating formulations. FIG. 1 illustrates the test pack card with adhered coated film strips. The center showed the lowest electric resistance change while the outside strips showed high electric resistance, indicating the presence of "air pocket" in the center. The electric resistance change along the diagonal line was in accordance with the yellow circle observed from the control chemical indicator sheet in an unmodified test pack. As an additional control, the same experiment was carried out using coated film strips without printed aluminum wires and these results are provided in Table 4. There is little change in resistance on the strips without aluminum wires between the pass and fail cycles compared to the resistance before sterilization (0.1-0.2 MΩ), indicating the aluminum wire played a role in detecting the air pocket.

TABLE 2

Formulations for PANI/PU system.

| Component | Formulation 8 | Formulation 9 | Formulation 10 |
|---|---|---|---|
| 30% PANI (g) | 1 | 1 | 1 |
| 25% N3390 (g) | 1.642 | 1.3632 | 1.3632 |
| 25% CAPA 3031 (g) | 0.637 | 0.744 | 0.9555 |
| Resistance (MΩ) | 1.4 | 0.35 | 0.9 |

TABLE 3

Electric resistance before and after a "fail" sterilization cycle (in MΩ).

| | Formulation 8 | Formulation 9 | Formulation 10 |
|---|---|---|---|
| Strip 1 (center) | 1.4 | 0.35 | 0.9 |
| Strip 2 | 15 | 0.6 | 1.9 |
| Strip 3 | 27 | 18 | 2.2 |
| Strip 4 | 19 | 22 | 6.2 |
| Strip 5 | >50 | 30 | 9.1 |

TABLE 3-continued

| | Electric resistance before and after a "fail" sterilization cycle (in MΩ). | | |
|---|---|---|---|
| | Formulation 8 | Formulation 9 | Formulation 10 |
| Strip 6 (outer edge) | >50 | 21 | 24 |
| Resistance before sterilization | 0.4 | 0.4 | 0.6 |

TABLE 4

| Electrical resistance change for PANI coated film without aluminum lines. | | |
|---|---|---|
| Strip # (from | Resistance after sterilization (MΩ) | |
| center to outer corner) | Fail | Pass |
| 1 | 0.06 | 0.4 |
| 2 | 0.05 | 0.3 |

TABLE 4-continued

| Electrical resistance change for PANI coated film without aluminum lines. | | |
|---|---|---|
| Strip # (from | Resistance after sterilization (MΩ) | |
| center to outer corner) | Fail | Pass |
| 3 | 0.06 | 0.25 |
| 4 | 0.06 | 0.25 |
| 5 | 0.08 | 0.25 |
| 6 | 0.06 | 0.1 |
| 7 | 0.03 | 0.08 |
| Resistance before sterilization | 0.12 | 0.34 |

Example 3. Conductivity Study in Bowie-Dick Pack With 2-Step Coating Approach Using the same PET film with printed aluminum wires, 30% PANI solution (PANI:DNNSA=1:1.5) in toluene was coated using a #22 Myer bar and then dried at 80° C. for 10 min. The resulting coating was then dipped into isopropanol for 10 seconds and dried for 10 min at 80° C. These samples were then coated with a second layer containing one of Formulations 11-13 as shown in Table 5. Each second coating solution was applied with a #12 Meyer bar and cured at 140° C. for 10 min. The twice-coated film with printed aluminum wires was then cut into rectangular strips as described in Example 2 and attached to a BD card diagonally as shown in FIG. 1. Electric resistance between the two printed aluminum wires were measured by piercing through the top coating to contact the underlying PANI-containing layer. An ISO INADQ 132 cycle was run. After sterilization, the resistance was measured again as shown in Table 6. The same electric resistance "air pocket" was detected in the BD test pack where the center strips showed minimum resistance change.

TABLE 5

| Formulations of upper (second) coating layer for 2-step PANI/PU system. | | | |
|---|---|---|---|
| Component | Formulation 11 | Formulation 12 | Formulation 13 |
| 30% N3390 | 3.284 g | 3.284 g | 1.642 g |
| 30% CAPA 3031 | 1.274 g | 1.274 g | 0.637 g |
| BYK-SilClean-3700 | | 0.19 g | 0.1637 g |
| T12 catalyst | 0.012 g | 0.012 g | 0.012 g |

TABLE 6

| Strip resistance change before and after sterilization in BD test pack (in MΩ). | | | |
|---|---|---|---|
| Strip number | Film -Formulation 11 | Film - Formulation 12 | Film - Formulation 13 |
| Strip 1 (center) | 19 | 0.28 | 0.5 |
| Strip 2 | >50 | 0.15 | 4 |
| Strip 3 | >50 | 0.47 | 22 |
| Strip 4 | >50 | 20 | >50 |
| Strip 5 | >50 | >50 | >50 |
| Strip 6 (out-edge) | >50 | >50 | >50 |
| Resistance before sterilization | 1 | 0.1 | 0.4 |

Example 4. PANI:DNNSA Ratio Study

Two additional PANI:DNNSA polymers were prepared at ratios of 1:1.3 and 1:1.75 PANI:DNNSA and blended with polyurethane reagents based on Formulation 9 with varying concentration of PANI as shown in Table 7. The ratio between PANI:DNNSA significantly affected the conductivity. A lower ratio of PANI:DNNSA is preferred for building an electronic chemical sensor for sterilization monitoring.

TABLE 7

| The impact of PANI:DNNSA ratio on electrical resistance. | | | |
|---|---|---|---|
| PANI:DNNSA | PANI concentration | Conductivity (MΩ) | Conductivity (MΩ) after methanol wash |
| 1:1.75 | 25% | 25 | 2.2 |
| 1:1.75 | 20% | 22 | 2.8 |
| 1:1.75 | 15% | >50 | 10 |
| 1:1.5 | 25% | 1 | 0.15 |
| 1:1.5 | 20% | 1 | 0.22 |
| 1:1.5 | 15% | 2.3 | 0.48 |
| 1:1.3 | 20% | 0.16 | 0.13 |

Example 5. Sterilization Temperature and Time Effect

A 30% PANI/PU solution as described in Example 2 was used to coat PET film with printed aluminum electrodes. The coated strips were attached to a Bowie-Dick card and re-packed into a test pack as described before. All strips showed about 0.3 MΩ resistance before sterilization. Two sterilization times were examined, 3.5 and 10 minutes, both conducted at 121° C. The resistance of each strip was measured with a multimeter and recorded as shown in Table 8. These results show that the electric sensor based on the coated film strips is temperature and time sensitive.

TABLE 8

Electric resistance change for PANI coated aluminum electrodes at a lower sterilization temperature (121° C.).

| | 121° C./3.5 min | | 121° C./10 min | |
| Sample Number | Before Sterilization (MΩ) | After Sterilization (MΩ) | Before Sterilization (MΩ) | After Sterilization (MΩ) |
| --- | --- | --- | --- | --- |
| 1 | 0.4 | 2.2 | 0.26 | 15.6 |
| 2 | 0.3 | 4.5 | 0.22 | 20.7 |
| 3 | 0.3 | 3.6 | 0.21 | 11.2 |
| 4 | 0.4 | 5.6 | 0.27 | 17 |

Example 6. Type 2 e-Bowie-Dick Test Pack

A moisture-sensing Antenna Inlay with G2iM or G2iL RFID was cut along the out-loop and the PET cover on the antenna was removed and replaced with masking tape (3M Company, St Paul, MN). Subsequently, the RFID was coated at the location of the two aluminum electrodes near the antenna (FIG. 2a) with approximately one microliter of polyurethane solution according to Formulation 9. The coated RFID was dried at 140° C. for 10 min. The RFID tag was read with a ThingMagic Reader to detect the connectivity of the RFID tag. The reader reads as "connected" indicating the disrupted loop was connected through PANI coating. All coated tags showed "connected" after PANI coating (Table 9). The backing liner paper of the RFID tag was then peeled off and the RFID was attached onto a Bowie-Dick paper card and inserted into a test pack as shown in FIG. 2b. The stack of cards were then wrapped into a Bowie-Dick test pack as in the original package. These electronic Bowie-Dick test packs were then sterilized using an AMSCO steam sterilizer in both ISO ADQ and ISO INADQ cycles. After the sterilization cycle was completed, the pack was read again with the RFID reader. The reader reported as "Disconnected" indicating a successful (ADQ) sterilization cycle and "Connected" in an unsuccessful (INADQ) cycle, indicating an "air pocket" with gas leak or low vacuum pressure. Table 9 shows the RFID responses as read by the RFID reader.

TABLE 9

PANI-coated RFID responses from sterilization cycles.

| RFID coating method | Before sterilization | Cycle | After Sterilization |
| --- | --- | --- | --- |
| 1 ul dot coating (steam tape cover) | Connected | Fail | Connected |
| 1 ul dot coating (steam tape cover) | Connected | Pass | Disconnected |
| 1 ul dot coating (original PET cover) | Connected | Fail | Connected |
| 1 ul dot coating (original PET cover) | Connected | Pass | Disconnected |
| Bar coating (steam tape cover) | Connected | Fail | Connected |
| Bar coating (steam tape cover) | Connected | Pass | Disconnected |

TABLE 9-continued

PANI-coated RFID responses from sterilization cycles.

| RFID coating method | Before sterilization | Cycle | After Sterilization |
| --- | --- | --- | --- |
| Bar coating (Steam tape cover) | Connected | Fail | Connected |
| Bar coating (Steam tape cover) | Connected | Pass | Disconnected |

Example 7: Dry Heat Challenge Test

RFID tags were coated as described in Example 6 with the solution of Formulation 9 with varying solids content (diluted with 50/50 MIBK/xylene) according to Table 10. The samples were read and their conductivity measured before baking in a 140° C. oven for 30 minutes. After baking, the tags were measured and read again. Table 10 shows the results. The data show that PANI is well suitable to make a Type 2 Chemical Indicator which requires a challenge at 140° C. for 30 minutes.

TABLE 10

Dry heat test for PANI-coated RFID.

| Coating condition | Resistance before heating (MΩ) | RFID results before Heating | Resistance after heating at 140° C./ 30 min (MΩ) | RFID results After heating |
| --- | --- | --- | --- | --- |
| 20% Solid | 0.08 | Connected | 0.99 | Connected |
| 15% Solid | 0.11 | Connected | 0.16 | Connected |
| 10% Solid | 0.19 | Connected | 0.02 | Connected |

Example 8. H₂O₂ Sterilization Monitoring

RFID tags were coated using the procedure of Example 6 with solutions having different solids contents according to Table 11. A pure PANI solution was also used as a control. After the tags were read and their resistivity was measured, all tags were loaded into a plastic tray and sterilized in Sterrad 100S VHP sterilizer for a complete cycle (Advanced Sterilization Products, Irvine, CA). The tags were removed from the sterilizer and then measured and read again. Table 11 shows the results. The data shows that PANI can be used as an electronic chemical indicator for sterilization methods based on hydrogen peroxide.

TABLE 11

The resistance and RFID responses before and after VHP sterilization.

| Coating condition | Resistance before VHP Sterilization (MΩ) | RFID results before VHP Sterilization | Resistance after VHP (MΩ) | RFID results AFTER VHP Sterilization |
| --- | --- | --- | --- | --- |
| 5% PANI (no binder) | 1.4 | Connected | 2.4 | Connected |
| | 0.02 | Connected | 4.0 | Connected |
| | 0.3 | Connected | 3.2 | Connected |
| 20% solid | 0.15 | Connected | 9.0 | Disconnected |
| | 0.13 | Connected | 8.9 | Disconnected |
| | 0.18 | Connected | 6.4 | Connected |
| 15% solid | 0.25 | Connected | 9.0 | Disconnected |
| | 0.13 | Connected | 8.9 | Disconnected |
| | 0.11 | Connected | 9.0 | Disconnected |

TABLE 11-continued

The resistance and RFID responses
before and after VHP sterilization.

| Coating condition | Resistance before VHP Sterilization (MΩ) | RFID results before VHP Sterilization | Resistance after VHP (MΩ) | RFID results AFTER VHP Sterilization |
|---|---|---|---|---|
| 10% Solid | 0.26 | Connected | 9.0 | Disconnected |
| | 0.11 | Connected | 9.0 | Disconnected |
| | 0.12 | Connected | 9.0 | Disconnected |

Example 9: Variation of Electrode Metal

Using a vacuum vapor deposition process, 100 nm of four different metals (gold, silver, aluminum, and tin) were deposited on 4 mil PET film. A sample of silver-coated PET was prepared by Kilby I e-beam evaporating silver metal onto a PET substrate in an evaporation chamber to yield a 100 nm thick coating at a speed of 9.5 angstroms per second (Å/s). In a similar fashion, a 100 nm thick aluminum coating on PET was obtained at a speed of 10 Å/s, a 100 nm thick tin coating on PET was obtained at a speed of 35 Å/s, and a 100 nm thick gold coating on PET was obtained at a speed of 5.4 Å/s.

Each resulting metallized PET film was then coated with the PANI/PU coating solution described in Example 1 (Formulation 1) using a #22 Meyer bar. A control sample without a metal coating was also coated with PANI/PU solution. After curing at 140° C. for 10 minutes, the samples were cut into 1.2 inch×⅜ inch coupons. Two silver lines were draw one inch apart with a silver paint pen on the top of the PANI coating at both ends of the coupon. The coupons were attached to a paper Bowie-Dick card and sterilized at 132° C. for 3.5 minutes. The resistance of each couple was read with a multimeter. Table 12 shows the results. It was found that the resistance values of both aluminum and tin increased after sterilization process.

TABLE 12

Resistance of metal-coated PET film before and after sterilization.

| Metal | Resistance (before sterilization) | Resistance (After sterilization) |
|---|---|---|
| Au | 14 Ω | 1.8 Ω |
| Ag | 12 Ω | 1.5 Ω |
| Al | 14 kΩ | 440 kΩ |
| Sn | 13 kΩ | >50 MΩ |
| PET control | 60 kΩ | 77 kΩ |

Example 10: Impact of Binder on PANI Resistance Change

A 20% PANI solution in toluene was coated on a commercial ultra-clean aluminium foil (VWR brand) with a #22 Meyer bar. The coating was then dried at 100° C. for 10 minutes. The obtained PANI-coated aluminum foil was then steam sterilized at 132° C. for 3.5 minutes. It was observed that the PANI coating was green before sterilization and yellow after sterilization. The resistance values measured with a multimeter between any two points were more than 50 Me after sterilization, while the resistance before sterilization was less than 0.5 MΩ.

The samples were stored at room temperature at ambient conditions for three weeks. During this time, the yellow PANI-coated aluminum foil slowly converted back to green and the resistance values gradually reduced to a few MΩ, indicating that the redox state of a PANI coating without a binder is reversable and therefore would not be suitable for making a reliable sensor.

In a contrast, formulation 9 with a polyurethane binder was coated on the same aluminum foil. The resistance value after steam sterilization was relatively stable for more than 6 months, with only a minor resistance change (<1 MΩ).

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A sensor device comprising:
a sterilant-responsive switch comprising:
    a circuit;
    a conductive polymer having a first state and a second state, wherein the conductive polymer comprises a repeat unit of: aniline, acetylene, pyrrole, phenylene, phenylene vinylene, phenylene ethynylene, phenylene sulfide, fluorene, pyrene, azulene, naphthalene, carbazole, indole, thiophene, ethylene dioxythiophene, or combinations thereof, and
    a polymeric binder configured to maintain the conductive polymer in a second state; and
    wherein the sterilant-responsive switch connects the circuit in the first state and disconnects the circuit in the second state, and
    wherein the conductive polymer is capable of being converted from being in the first state to being in the second state when in contact with a sterilant.

2. The sensor device of claim 1, wherein the conductive polymer changes from a first impedance to a second impedance when an environmental change receptor or the sterilant contacts the conductive polymer.

3. The sensor device of claim 1, wherein the conductive polymer comprises a repeat unit of aniline, pyrrole, or combinations thereof.

4. The sensor device of claim 1, further comprising a first conductive trace and a second conductive trace, each having a first end electrically coupled to the circuit and a second end.

5. The sensor device of claim 4, wherein the sterilant-responsive switch modifies an electrical connection between the first conductive trace and the second conductive trace in response to a sterilization process.

6. The sensor device of claim 4, wherein the first conductive trace and the second conductive trace comprise a metal electrode.

7. The sensor device of claim 6, wherein the metal electrode comprises a metal, wherein the oxidation potential of the metal is greater than the reduction potential of the conductive polymer.

8. The sensor device of claim 6, wherein the metal electrode comprises aluminum, iron, zinc, tungsten, molybdenum, tin, nickel, copper, or alloys thereof.

9. The sensor device of claim 6, upon exposure to an adequate environmental condition comprising a steam sterilant, the metal electrode reacts with the conductive polymer to change impedance of the conductive polymer.

10. The sensor device of claim 1, wherein the sterilant-responsive switch is configured to change impedance in response to an adequate sterilization process.

11. The sensor device of claim 1, wherein the circuit is an integrated circuit.

12. The sensor device of claim 1, wherein polymeric binder comprises a polyurethane, a polyvinyl butyral, a polyacrylate, polyvinyl acetate, polystyrene, polystyrene acrylate, a polyurea, a polyimide, an amide, an epoxy, a glycidyl-Si—Zr-containing solgel, a polyester, a phenoxy resin, a polysulfide, or mixtures thereof.

13. A method, the method comprising:
providing the sensor device of claim 1;
exposing the sensor device to a sterilant in a sterilization process;
allowing the sterilant-responsive switch to react with the sterilant which changes the sterilant-responsive switch from the first state to the second state.

14. The method of claim 13, wherein the sterilant is at least 95% saturated steam and the adequate sterilization process is 134 degrees Celsius for 2 minutes or 121 degrees Celsius for 10 minutes.

15. A system, the system comprising:
the sensor device of claim 1;
a memory element to store data captured by the sensor device; and
a sensing device configured to interrogate the sensor device.

* * * * *